US011773328B2

(12) United States Patent
Osborne et al.

(10) Patent No.: US 11,773,328 B2
(45) Date of Patent: Oct. 3, 2023

(54) POWDERED COMPOSITION COMPRISING A FIREPROOFING AGENT

(71) Applicant: Firmenich SA, Satingy (CH)

(72) Inventors: Murray Osborne, Satigny (CH); Bhavesh Mandhane, Mumbai (IN)

(73) Assignee: FIRMENICH SA, Satigny (CH)

(*) Notice: Subject to any disclaimer, the term of this patent is extended or adjusted under 35 U.S.C. 154(b) by 0 days.

(21) Appl. No.: 16/766,237

(22) PCT Filed: Mar. 1, 2019

(86) PCT No.: PCT/EP2019/055091
§ 371 (c)(1),
(2) Date: May 21, 2020

(87) PCT Pub. No.: WO2019/170528
PCT Pub. Date: Sep. 12, 2019

(65) Prior Publication Data
US 2020/0392410 A1 Dec. 17, 2020

(30) Foreign Application Priority Data

Mar. 5, 2018 (EP) ..................... 18159982

(51) Int. Cl.
| | | |
|---|---|---|
| C09K 21/02 | (2006.01) | |
| A01K 1/015 | (2006.01) | |
| A61K 8/11 | (2006.01) | |
| A61K 8/25 | (2006.01) | |
| A61K 8/26 | (2006.01) | |
| A61K 8/92 | (2006.01) | |
| A61Q 5/02 | (2006.01) | |
| A61Q 15/00 | (2006.01) | |
| C09K 21/06 | (2006.01) | |
| C11D 3/12 | (2006.01) | |
| C11D 3/22 | (2006.01) | |
| C11D 3/50 | (2006.01) | |
| C08K 3/34 | (2006.01) | |
| C08K 3/016 | (2018.01) | |
| C09K 21/14 | (2006.01) | |

(52) U.S. Cl.
CPC ............ *C09K 21/02* (2013.01); *A01K 1/0152* (2013.01); *A61K 8/11* (2013.01); *A61K 8/25* (2013.01); *A61K 8/26* (2013.01); *A61K 8/92* (2013.01); *A61Q 5/02* (2013.01); *A61Q 15/00* (2013.01); *C09K 21/06* (2013.01); *C09K 21/14* (2013.01); *C11D 3/126* (2013.01); *C11D 3/222* (2013.01); *C11D 3/505* (2013.01); *A61K 2800/412* (2013.01); *A61K 2800/56* (2013.01)

(58) Field of Classification Search
None
See application file for complete search history.

(56) References Cited

U.S. PATENT DOCUMENTS

| | | | | |
|---|---|---|---|---|
| 4,952,400 A | * | 8/1990 | Tararuj ............... | A45D 40/0087 |
| | | | | 434/377 |
| 5,391,374 A | | 2/1995 | Charbonneau et al. | |
| 5,445,821 A | * | 8/1995 | Brown .................. | A61Q 13/00 |
| | | | | 428/905 |
| 5,508,259 A | | 4/1996 | Holzner et al. | |
| 7,204,998 B2 | * | 4/2007 | Holzner ................. | A23L 27/72 |
| | | | | 424/490 |
| 2009/0047434 A1 | * | 2/2009 | Trophardy ............. | A23L 27/72 |
| | | | | 427/377 |
| 2009/0253612 A1 | * | 10/2009 | Mushock ............... | C11D 3/505 |
| | | | | 512/4 |
| 2012/0094049 A1 | * | 4/2012 | Killough ................ | C08K 3/016 |
| | | | | 524/451 |
| 2014/0056955 A1 | * | 2/2014 | Gadient ............... | A23K 20/174 |
| | | | | 424/401 |
| 2014/0079747 A1 | | 3/2014 | Dihora et al. | |
| 2015/0202127 A1 | * | 7/2015 | Hara ...................... | A61Q 15/00 |
| | | | | 424/401 |

FOREIGN PATENT DOCUMENTS

| | | |
|---|---|---|
| EP | 2300146 A1 | 3/2011 |
| EP | 2579976 A1 | 4/2013 |
| JP | S5885809 A | 5/1983 |
| JP | S5885809 U | 6/1983 |
| JP | S6054308 A | 3/1985 |
| JP | S6085809 U | 6/1985 |
| JP | 2000008041 A | 1/2000 |
| JP | 2005509698 A | 4/2005 |

(Continued)

OTHER PUBLICATIONS

Jadhav, N. R., et al. "Talc: A versatile pharmaceutical excipient." World Journal of Pharmacy and Pharmacutical Sciences 2 (2013): 4639-4660. (Year: 2013).*

Singh, M. N., et al. "Microencapsulation: A promising technique for controlled drug delivery." Research in pharmaceutical sciences 5.2 (2010): 65-77. (Year: 2010).*

Lengyel, Miléna, et al. Microparticles, Microspheres, and Microcapsules for Advanced Drug Delivery. Scientia Pharmaceutica. 2019; 87(3):20. https://doi.org/10.3390/scipharm87030020 (Year: 2019).*

International Search Report and Written Opinion for corresponding PCT/EP2019/055091 dated Jun. 4, 2019, 11 pages.

*Primary Examiner* — Bethany P Barham
*Assistant Examiner* — Peter Anthopolos
(74) *Attorney, Agent, or Firm* — Armstrong Teasdale LLP

(57) ABSTRACT

The present disclosure relates to the field of delivery systems. Described herein is a powdered composition comprising including granules having a hydrophobic active ingredient dispersed in a polymeric matrix, wherein the powdered composition contains a fireproofing agent. The fireproofing agent defined in the present disclosures includes talc that, when present in the powdered composition, prevents a dust explosion risk when the powdered composition is manufactured, handled or dosed into a consumer product.

12 Claims, No Drawings

(56) References Cited

FOREIGN PATENT DOCUMENTS

| | | |
|---|---|---|
| JP | 2005521767 A | 7/2005 |
| JP | 2013051964 A | 3/2013 |
| JP | 2014051457 A | 3/2014 |
| WO | 03043728 A1 | 5/2003 |
| WO | 03082965 A1 | 10/2003 |
| WO | 2007004166 A1 | 1/2007 |
| WO | 2013068255 A1 | 5/2012 |
| WO | 2013092375 A1 | 6/2013 |
| WO | WO-2014186740 A2 * | 11/2014 ........... A61K 8/0241 |
| WO | 2015110568 A1 | 7/2015 |
| WO | 2017134179 A1 | 8/2017 |

* cited by examiner

POWDERED COMPOSITION COMPRISING A FIREPROOFING AGENT

CROSS-REFERENCE TO RELATED APPLICATIONS

This application is a U.S. National Phase Application of PCT/EP2019/055091, filed on Mar. 1, 2019, which claims the benefit of priority to European Patent Application Number 18159982.0, filed Mar. 5, 2018, the entire contents of which are hereby incorporated by reference herein.

TECHNICAL FIELD

The present invention relates to the field of delivery systems. It concerns more particularly a powdered composition comprising granules having a perfume oil or a flavor oil dispersed in a polymeric matrix, wherein the powdered composition contains a fireproofing agent. The fireproofing agent defined in the present invention comprises talc that prevents a dust explosion risk when said composition is manufactured, handled or dosed.

BACKGROUND OF THE INVENTION

Microcapsules are employed to a large extent in the perfumery and flavouring industries. They constitute delivery systems for perfuming or flavouring ingredients and can be advantageously used in a very large number of applications. The encapsulation of active substances such as perfuming or flavouring ingredients provides at the same time a protection of the ingredients there-encapsulated against "aggressions" such as oxidation or moisture and allows, on the other hand, a certain control of the kinetics of flavour or fragrance release to induce sensory effects through sequential release.

Now, the numerous advantageous properties of microcapsules in these fields are opposed to other properties that must be taken into account during their preparation, transportation, storage and handling, especially when those microcapsules are in a powdered form (referred as granules). In fact, such delivery systems, due to their nature, and in particular to the fact that they encapsulate volatile and flammable substances, constitute combustible dusts which can, when dispersed in air or another oxygen-containing gas, form readily ignitable mixtures. Those granules have unfortunately a tendency to explode. This issue becomes important not only during the preparation of the granules but also during manipulation of the granules in the factory environment for preparing a consumer product in which such granules are added.

One of the parameter to know the dangerous properties of a product is the constant, $K_{St}$ that represents the maximum explosion behaviour of a combustible dust in a closed system.

There is a well-established correspondence between the value of constant $K_{St}$ and dust hazard classes: from St-1 (low explositvity) to St-3 (high explosivity).

It has to be noticed that the classification of a dust into one of the classes St-1 to St-3 is a statement of explosion violence only. It gives no indication of the ignition sensitivity of a dust or the probability of a dust explosion during the manipulation of granules once formed, most of the time by spray-drying.

That is why, another parameter the Minimum Ignition Energy (MIE) has also to be taken account when a hazard analysis is conducted on a powdered material to assess the explosion risk.

The MIE of a dust is defined as the lowest quantity of electrical energy stored in a capacitor which, when discharged over a spark gap, is just not sufficient to ignite the most readily ignitable dust or air mixture in a series of ten consecutive tests, at atmospheric pressure, ambient temperature and lowest turbulence possible. The MIE is indicative of the likelihood of ignition of a dust cloud by discharges of static electricity or other such ignition sources. MIE is measured in joules (J).

Components having a very low MIE value mean that a very low amount of energy is sufficient to initiate an explosion.

A test protocol is described in ASTM-E2019, VDI-2263, Center for Chemical Process Safety CCPS Publication G-95, *Guidelines for Safe Handling of Powders and Bulk Solids* © 2005 by the American Institute of Chemical Engineers, and the Operating Instructions for the MIKE-3 apparatus (manufactured by Kühner A G, Birsfelden, C H), by C. Cesana and R. Siwek.

It is known from the prior art that certain compounds (called fireproofing agents) can minimize the explosion risk of a powdered composition.

WO03/043728A1 discloses perfuming or flavouring granules having fireproofing agents dispersed in or absorbed within a polymeric carrier material. However, the fireproofing agents disclosed in this document have to be used in a large amount compared to the amount of granules.

Furthermore, depending on the storage conditions, granules can be subjected to high humidity conditions and have to be stable on a long term.

There is therefore a need to provide a cost-effective and stable powdered composition that could be manufactured and/or handled under safety conditions.

The powdered composition of the invention solves this problem as it comprises talc as a fireproofing agent that prevents explosion risk of granules (made of an oily phase dispersed in a water soluble polymer matrix) during their preparation and/or handling.

DESCRIPTION OF THE INVENTION

Surprisingly, it has been found that the presence of a new fireproofing agent comprising talc in a powdered composition could reduce the violence of possible explosions. It has notably been shown that talc could be blended directly with granules in an amount effective to reduce the violence of possible explosions during handling and dosing in the factory environment. The MIE value of the powdered composition comprising the new fireproofing agent could thus be effectively increased without using a high amount of talc compared to the amount of granules.

Very surprisingly, this new explosion suppressant also reduces the hygroscopicity of powders comprising the granules of the present invention since a low amount, or even no anti-caking agent need to be added during the preparation of the powdered composition to obtain a stable composition under high humidity conditions.

The present invention therefore provides a powdered composition that is cost effective, stable at high temperature and under high humidity conditions and that can be manufactured and/or handled with safety.

Thus, a first object of the invention is a powdered composition comprising at least one dried granule, wherein the granule comprises a perfume oil or a flavour oil dispersed in a polymeric matrix, characterized in that the powdered composition contains a fireproofing agent comprising talc.

A second object of the invention is a process for preparing a powdered composition as defined above comprising the steps of dry blending a fireproofing agent comprising talc with granules comprising a perfume oil or a flavour oil dispersed in a polymeric matrix to form a powdered composition.

A third object of the invention is a process for preparing a powdered composition as defined above comprising the steps of adding a fireproofing agent comprising talc to an aqueous emulsion of a perfume oil or a flavor oil in a water soluble polymer and spray-drying the obtained emulsion to form a powdered composition.

Another object of the invention is the use of a fireproofing agent comprising talc in a powdered composition comprising granules made of a polymer matrix and a perfume or a flavour oil dispersed in said matrix for reducing the violence of the explosion of the composition during its manipulation.

A last object of the invention is a powdered consumer product, preferably in the form of a dry shampoo, talcum powder, powder detergent, detergent beads, solid scent booster, cat litter, powder hair dye, antiperspirant composition, deodorant composition, comprising the powdered composition as defined above.

DETAILED DESCRIPTION OF THE INVENTION

Unless stated otherwise, percentages (%) are meant to designate percent by weight of a composition.

"Granule" defined in the present invention refers to a delivery system comprising a hydrophobic active ingredient dispersed in a polymeric matrix. According to the invention, the hydrophobic active ingredient comprises a perfume oil or a flavour oil which can be encapsulated in core-shell microcapsules and/or freely dispersed (i.e not encapsulated in core-shell microcapsules) in the matrix.

"Microcapsule" or "core-shell microcapsule" (which are used indifferently in the present invention) refers to a delivery system comprising an oil-based core of a hydrophobic active ingredient encapsulated by a polymeric shell.

It should be understood that according to specific embodiments, granules can comprise microcapsules when at least one part of the oil phase dispersed in the matrix is encapsulated in microcapsules.

According to the invention, "non-encapsulated oil" refers to oil that is simply entrapped (or freely dispersed) within the polymeric matrix but that is not encapsulated in a microcapsule.

By contrast, according to the invention, "encapsulated oil" refers to oil that is encapsulated in a microcapsule.

Non encapsulated oil comprises a first hydrophobic active ingredient and the encapsulated oil comprises a second hydrophobic active ingredient that can be the same or can differ from the first hydrophobic active ingredient.

According to the invention, the wordings "mean diameter" or "mean size" are used indifferently.

Mean sizes d(v, 0.5) are measured by a laser diffraction particle size analyzer.

The present invention has now found a way of reducing the violence of the explosion of a powdered composition possibly induced by its suspension in the air during its preparation or during its handling thanks to the use of a fireproofing agent comprising talc. This is very advantageous considering that such delivery systems are mainly composed of highly volatile ingredients which constitute therefore combustible dusts.

Furthermore, the powdered composition of the invention has proved to be less sensitive to ignition, i.e. to present a reduced tendency to explode. This characteristic may be measured and is expressed through the minimum ignition energy or MIE parameter.

Powdered Composition

A first object of the invention is therefore a powdered composition comprising at least one dried granule, wherein the granule comprises a perfume oil or a flavour oil dispersed in a polymer matrix, characterized in that the powdered composition contains a fireproofing agent comprising talc.

According to an embodiment, the powdered composition has a minimum ignition energy (MIE) value of 300 mJ or greater than 300 mJ. One can consider that a powdered composition having a MIE≥300 mJ is not ignited by electric discharges.

One of the essential features of the present invention is that the powdered composition comprises talc as a fireproofing agent.

The fireproofing agent can be added in addition to the dried granules to form the powdered composition (a blend of granules and talc is thus formed) and/or can be present in the granules within the polymeric matrix. The latter presents rather a benefit for the safety regarding the preparation of the granules themselves whereas the former presents rather a benefit for the safety regarding the handling and dosage of the granules into a consumer product.

According to an embodiment, the powdered composition comprises:
(i) at least one dried granule, wherein the granule is made of a perfume oil or a flavour oil dispersed in a polymeric matrix, and
(ii) a fireproofing agent comprising talc;
wherein the weight ratio between the granule and talc in the powdered composition is comprised between 10:90 to 90:10, preferably between 30:70 and 60:40, and more preferably between 40:60 and 55:45.

According to another embodiment, the powdered composition comprises at least one granule made of:
a polymeric matrix,
an oil phase comprising a perfume oil or a flavour oil dispersed in said matrix
wherein the fireproofing agent comprising talc is dispersed within the polymeric matrix.

The granule defined in the invention is based on the presence of an oil phase comprising at least a perfume oil or a flavour oil dispersed in a water soluble polymer matrix.

"By dispersed in a water soluble polymer matrix", it is meant that the oil phase is dispersed within the matrix in a non-encapsulated form (freely dispersed) and/or is dispersed within the matrix in an encapsulated form (encapsulated in microcapsules).

Granules defined in the invention have preferably a mean particle size greater than 15 microns, more preferably between 35 and 300 microns.

According to an embodiment, at least one part of the oil phase is freely dispersed in the matrix (i.e not encapsulated in microcapsules).

According to a particular embodiment, the totality of the oil phase is not encapsulated in core-shell microcapsules (i.e freely dispersed in the matrix).

According to another embodiment, at least one part of the oil phase is encapsulated in microcapsules. According to a particular embodiment, at least one part of the oil phase is encapsulated in microcapsules and at least one part is not encapsulated in core-shell microcapsules (i.e freely dispersed in the matrix).

According to another particular embodiment, the totality of the oil phase is encapsulated in microcapsules.

Hydrophobic Active Ingredient

By "hydrophobic active ingredient", it is meant any active ingredient—single ingredient or a mixture of ingredients—which forms a two-phases dispersion when mixed with water.

In a preferred aspect of the invention, the hydrophobic active ingredient is defined by a log P above 1, more preferably above 2.

Preferably, the hydrophobic active ingredient comprises at least 90% by weight, relative to the total weight of the hydrophobic active ingredient, of compounds having a log P of at least 1, more preferably it comprises at least 90% by weight of ingredients having a log P of at least 2. Even more preferably, the hydrophobic active ingredient comprises at least 99% by weight, relative to the total weight of the hydrophobic active ingredient, of ingredients having a log P of at least 1, most preferably it comprises at least 99% by weight of ingredients having a log P of at least 2. For the purpose of the present invention log P is defined as the calculated log P as obtained by calculation using the EPI suite v3.10, 2000, U.S. Environmental Protection Agency.

According to the invention, the hydrophobic active ingredient comprises a perfume oil or a flavor oil. For the purpose of the present invention, the terms "flavour or fragrance" encompass flavour or fragrance ingredients or compositions of current use in the flavour and/or fragrance industry, of both natural and synthetic origin. It includes single compounds and mixtures. Specific examples of such flavour or fragrance ingredients may be found in the current literature, e.g. in Fenaroli's Handbook of flavour ingredients, 1975, CRC Press; Synthetic Food adjuncts, 1947 by M. B. Jacobs, edited by Van Nostrand; or Perfume and Flavor Chemicals by S. Arctander, 1969, Montclair, N.J. (USA). Many other examples of current flavouring and/or perfuming ingredients may be found in the patent and general literature available. The flavouring or perfuming ingredients may be present in the form of a mixture with solvents, adjuvants, additives and/or other components, generally those of current use in the flavours and fragrance industry.

"Flavouring ingredients" are well known to a person skilled in the art of aromatising as being capable of imparting a flavour or taste to a consumer product, or of modifying the taste and/or flavour of said consumer product, or yet its texture or mouthfeel.

By "perfuming ingredients" it is understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface. It also contains malodor counteracting ingredients and compositions. By the term "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor. Accordingly, in an embodiment, the hydrophobic active ingredient comprises at least 5 wt. %, preferably at least 10.%, preferably at least 20%, more preferably at least 30% and most preferably at least 40% of chemical compounds having a vapour pressure of at least 0.007 Pa at 25° C., preferably at least 0.1 Pa at 25° C., more preferably at least 1 Pa at 25° C. and most preferably at least 10 Pa at 25° C., all percentages being defined by weight relative to the total weight of the hydrophobic active ingredient. Compounds meeting these criteria are generally regarded as having a volatile character and therefore have an odor or flavour. The method of the present invention therefore allows efficient encapsulation of high amounts of volatile ingredients. In a preferred embodiment of the invention, the hydrophobic active ingredient does not comprise any compound that remains odorless due to a volatility below any of the above-mentioned thresholds.

For the purpose of the present invention the vapour pressure is determined by calculation. Accordingly, the method disclosed in "EPI suite"; 2000 U.S. Environmental Protection Agency, is used to determine the value of the vapour pressure of a specific compound or component of the hydrophobic active ingredient.

The amount of hydrophobic active ingredient in the powdered composition is preferably comprised between 10 and 90% by weight, more preferably between 15 and 60% by weight, relative to the total weight of the composition.

According to a particular embodiment, at least one part of the oil phase is encapsulated in core-shell microcapsules, preferably in an amount comprised between 3 and 70%, preferably between 5 and 50%, based on the total weight of the granules.

Core-Shell Microcapsules (when Present)

Core-shell microcapsules defined in the present invention comprise a polymeric shell and an oil-based core comprising a perfume oil or a flavour oil.

The nature of the polymeric shell of the microcapsules of the invention can vary. As non-limiting examples, the shell can be made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall, and mixtures thereof.

According to an embodiment, the shell of the microcapsule is based on melamine formaldehyde resin or melamine formaldehyde resin cross-linked with at least one polyisocyanate or aromatic polyols.

According to another embodiment, the shell of the microcapsule is polyurea-based.

The shell can also be a hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:
1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 and WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of polyacrylate (and copolymers especially with acrylamide), gum arabic, soy protein, gelatin, sodium caseinate and mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula

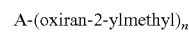

A-(oxiran-2-ylmethyl)$_n$ wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to another embodiment, the shell of the microcapsule is polyurea- or polyurethane-based. Examples of processes for the preparation of polyurea- and polyurethane-based microcapsule slurry are for instance described in WO2007/004166, EP 2300146, EP2579976 the contents of which is also included by reference. Typically a process for the preparation of polyurea- or polyurethane-based microcapsule slurry include the following steps:
a) dissolving at least one polyisocyanate having at least two isocyanate groups in an oil to form an oil phase;
b) preparing an aqueous solution of an emulsifier or colloidal stabilizer to form a water phase;
c) adding the oil phase to the water phase to form an oil-in-water dispersion, wherein the mean droplet size is comprised between 1 and 500 μm, preferably between 5 and 50 μm;

d) applying conditions sufficient to induce interfacial polymerisation and form microcapsules in form of a slurry.

According to the invention, it should be understood that, after encapsulation, whatever the nature of the microcapsule(s), the internal core of the capsule is only made of the core oil composed of a perfume oil.

The granules defined in the present invention can contain microcapsules which can vary by the core perfume oil inside them and/or by the wall (different chemistries or same chemistries but different process parameters like cross-linking temperature or duration).

According to a particular embodiment of the invention, the microcapsules have an outer coating selected from the group consisting of a non-ionic polysaccharide, a cationic polymer and mixtures thereof.

Such coating will help drive capsule deposition and retention on substrate during the wash process so that a significant part of the capsules which have not been broken in the wash phase/upon lathering would transfer to the substrate (skin, hair fabrics) and be available for perfume release when the capsules are broken upon rubbing after drying.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 2M Dalton, more preferably between 50,000 and 3.5M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C135 or C17, origin Rhodia).

Polymeric Matrix

The polymeric matrix defined in the present invention is a water-soluble polymer matrix.

Any water soluble polymer can be used for the purpose of the invention.

A "water soluble polymer" is intended for the purpose of the present invention as encompassing any polymer which forms a one-phase solution in water. Preferably, it forms a one phase solution when dissolved in water at concentrations as high as 20% by weight, more preferably even as high as 50% by weight. Most preferably it forms a one phase solution when dissolved in water at any concentration.

Preferably, the water-soluble polymer comprises carbohydrates. For example, the water-soluble polymer comprises mono-, oligo- and/or polysaccharides, wherein the prefixes oligo- and poly are as defined below.

In an embodiment of the present invention, the water-soluble polymer comprises a monomeric, oligomeric or polymeric carrier material, or mixtures of two or more of these. An oligomeric carrier is a carrier wherein 2-10 monomeric units are linked by covalent bonds. For example, if the oligomeric carrier is a carbohydrate, the oligomeric carrier may be sucrose, lactose, raffinose, maltose, trehalose, fructo-oligosaccharides, to name a few examples only.

Examples of a monomeric carrier materials are glucose, fructose, mannose, galactose, arabinose, fucose, sorbitol, mannitol, for example.

Polymeric carriers have more than 10 monomeric units that are linked by covalent bonds. Non limiting examples of the latter include polyvinyl acetate, polyvinyl alcohol, dextrines, maltodextrines, natural or modified starch, vegetable gums, pectins, xanthanes, alginates, carragenans or yet cellulose derivatives such as for example carboxymethyl cellulose, methylcellulose or hydroxyethylcellulose, and generally all materials currently used for encapsulation of volatile substances. Preferably, the polymeric carrier comprises maltodextrin. Most preferably it comprises maltodextrin and modified starch, such as, for example, alkenyl-succinated starch.

The polymeric matrix is preferably present in an amount between 25 and 50% by weight, based on the total weight of the granule.

Fireproofing Agent

The powdered composition of the invention is notably characterized by the fact that it contains a fireproofing agent comprising talc. In a particular embodiment, the fireproofing agent consists of talc.

According to another embodiment, talc is used in combination with another fireproofing agent chosen in the group consisting of sodium carbonate, zeolite, sodium sulphate, and mixtures thereof.

Without being bound by any theory, the Applicant is of the opinion that according to the embodiment where talc is present as a blend with the granules, talc can cover the surface of the granules in a dust cloud and therefore reducing the explosion risk.

Thus, according to an embodiment, talc has a mean particle size lower than the mean particle size of the granules. Preferably, talc has a mean particle size comprised between 5 and 50 microns, preferably between 10 and 20 microns.

Anticaking-Agent

The powdered composition can comprise an anti-caking agent, preferably hydrophobic and/or hydrophilic silica to increase the flowability of the powder.

Since the powdered composition shows a good stability under humid conditions, only a few amount, or even no amount of an anti-caking agent is needed.

According to a particular embodiment, the amount of the anti-caking agent in the powdered composition is comprised between 1 and 15% by weight, preferably between 2.5 and 10% by weight, based on the total weight of the composition.

According to another particular embodiment, the powdered composition is free from any anti-caking agent.

Process for the Preparation of the Powdered Composition

Embodiments described for the powdered composition also apply for the process for the preparation of said composition.

There are several alternatives for preparing the powdered composition as defined in the invention.

According to an embodiment, when talc is present as a blend with the granules, the process for preparing a powdered composition comprises the steps of dry blending a fireproofing agent comprising talc with granules comprising a perfume oil or a flavour oil dispersed in a polymer matrix to form a powdered composition.

After the dry blending, granules are covered by a layer of talc that prevents explosion risk of granules during the manipulation of the obtained powdered composition (in the form of a bend).

There is no limitation regarding the way to obtain the dried granules.

Among those methods, one may cite for example the spray-drying that is well-known method for the encapsulation of active ingredient.

However, one may cite also other drying method such as the extrusion, the fluidized bed, or even a drying at room temperature using materials (carrier, desiccant) that meet specific criteria (see for example WO2017134179).

According to an embodiment, the composition contains spray-dried granules obtained by a process comprising the steps of spray-drying an aqueous emulsion of a perfume oil or a flavour oil in a water soluble polymer.

More particularly, when the oil phase comprises at least one part that is freely dispersed in the matrix, dried granules are obtained by a process comprising the steps of
(i) Preparing a water phase comprising a water soluble polymer,
(ii) Preparing an oil phase comprising a perfume oil or a flavour oil; and mixing the oil phase with the water phase to obtain an emulsion;
(iii) Optionally, mixing the emulsion of step (ii) with a microcapsule slurry comprising at least a microcapsule having an oil-based core and a polymeric shell; and
(iv) Drying, preferably spray-drying the slurry of step (iii) to obtain spray-dried granules, When the oil phase comprises at least one part that is encapsulated in the matrix, dried particles are obtained by a process comprising the steps of
(i) Preparing a water phase comprising a water soluble polymer,
(ii) Optionally, preparing an oil phase comprising a perfume oil or a flavour oil; and mixing the oil phase with the water phase to obtain an emulsion;
(iii) Mixing the water phase of step (i) or the emulsion of step (ii) with a microcapsule slurry comprising at least a microcapsule having an oil-based core and a polymeric shell; and
(iv) Drying, preferably spray-drying the slurry of step (iii) to obtain spray-dried granules.

According to a particular embodiment, an anticaking agent, is added during step (iii) and/or step (iv) and/or after step (iv) of the process described above.

According to another embodiment, when talc is present in the granules, the process for preparing a powdered composition comprises the steps of adding a fireproofing agent comprising talc to an aqueous emulsion of a perfume oil or a flavor oil in a water soluble polymer and spray-drying the obtained emulsion to form a powdered composition.

Powdered compositions obtained by the processes described in the above embodiments are also objects of the invention.

Method for Reducing the Violence of the Explosion of a Powdered Composition

Another object of the invention is the use of talc in a powdered composition comprising granules made of a polymeric matrix and a perfume or a flavour oil dispersed in said matrix for reducing the violence of the explosion of the composition during its manipulation.

Another object of the invention is a method for reducing violence of explosion of a powdered composition comprising granules made of a polymeric matrix and a perfume or a flavour oil dispersed in said matrix, the method comprising the steps of:
  adding to the powdered composition a fireproofing agent comprising talc, and/or,
  incorporating the fireproofing agent comprising talc in and/or within granules of the powdered composition, and/or,
  blending the fireproofing agent comprising talc with the powdered composition.

Powdered Consumer Product

The invention's microcapsules can advantageously be used in many application fields and used in consumer products. Microcapsules can be used in powder form, applicable to powdered consumer products.

A consumer product, preferably in the form of a laundry care product, a home care product, a body care product, a skin care product, a hair care product, an air care product, or a hygiene product, comprising microcapsules as defined above, or a perfuming composition as defined above is also an object of the present invention.

Another object of the present invention is a powdered consumer product comprising
(a) from 2 to 65% by weight, relative to the total weight of the consumer product, of at least one surfactant;
(b) powdered composition as defined above.
(c) optionally perfume powder that is different from the microcapsules defined above is also an object according to the present invention.

According to a particular embodiment, the consumer product is selected from the group consisting of a dry shampoo, talcum powder, powder detergent, detergent beads, solid scent booster, cat litter, powder hair dye, antiperspirant composition, deodorant composition.

Preferably, the consumer product comprises from 0.05 wt %, preferably from 0.1 to 15 wt %, more preferably between 0.2 and 5 wt % of the powdered composition of the present invention, these percentages being defined by weight relative to the total weight of the consumer product. Of course the above concentrations may be adapted according to the olfactive effect desired in each product.

The invention will be now illustrated but not limited by way of the following examples

Example 1

Process for Preparing a Powdered Composition Comprising a Fireproofing Agent A—Preparation of Granules a Having an Oil Phase Freely Dispersed in the Polymeric Matrix An emulsion of the following composition was spray-dried in a spray-drier Büchi (origin: Switzerland) (with an air inlet temperature set to 215° C. and a throughput set to 500 ml per hour. The air outlet temperature was of 105° C.) to obtain spray-dried granules having the following composition (see Table 1).

TABLE 1

Composition of the spray-dried granules A

| Ingredients | Granules A |
|---|---|
| Perfume A | 48 |
| Modified starch | 27.5 |
| Maltose | 17.5 |
| Tripotassium Citrate | 4.3 |
| Citric acid | 2.2 |
| Silica | 0.5 |
| | 100% |

TABLE 2

Composition of Perfume A

| Component | % |
|---|---|
| 4-(1,1-DIMÉTHYLÉTHYL)-1-CYCLOHEXYLE ACETATE[1] | 14.50 |
| LINALOL BJ | 10.50 |
| LILIAL ®[2] | 10.00 |
| ISO E SUPER[3] | 10.00 |
| CITRONELLYL NITRILE | 9.00 |
| DIPHENYLOXYDE | 6.50 |
| ISOBORNYL ACETATE | 6.00 |
| BETA IONONE | 6.00 |
| TRICYCLO[5.2.1.0~2,6~]DEC-3-EN-8-YL ACETATE (A) + TRICYCLO[5.2.1.0~2,6~]DEC-4-EN-8-YL ACETATE (B)[4] | 5.50 |
| ETHER MT | 4.00 |
| HEDIONE ®[5] | 4.00 |
| GERANIOL 60 | 3.00 |
| CITRAL | 2.50 |
| ALDEHYDE C 10 | 2.50 |
| ALLYL HEPTANOATE | 2.50 |
| ETHYL METHYL-2-BUTYRATE | 1.50 |
| GERANYL ACETATE | 1.00 |
| 2,4-DIMETHYL-3-CYCLOHEXENE-1-CARBALDEHYDE[6] | 1.00 |

[1] Firmenich SA, Switzerland
[2] 3-(4-tert-butylphenyl)-2-methylpropanal, Givaudan SA, Vernier, Switzerland
[3] 1-(octahydro-2,3,8,8-tetramethyl-2-naphtalenyl)-1-ethanone, International Flavors & Fragrances, USA
[4] Firmenich SA, Switzerland
[5] Methyl dihydrojasmonate, Firmenich SA, Switzerland
[6] Firmenich SA, Switzerland B—Preparation of Granules B Having an Oil Phase Partly Encapsulated in Core-Shell Microcapsules.

TABLE 3

Composition of slurry of core-shell microcapsules 1

| Ingredient | [%] |
|---|---|
| Oil Phase | 30.9 |
| Perfume oil[a] | 30.28 |
| trimethylol propane adduct of xylylene diisocyanate[1] | 0.62 |
| Water phase | 69.1 |
| Acrylamide and acrylic acid copolymer[2] | 4.7 |
| Melamine-formaldehyde resins[3] | 2.45[3] |
| Water | 50.55 |
| Sodium hydroxide | 0.5 |
| Acetic acid | 0.2 |
| acrylamidopropyltrimonium chloride/acrylamide copolymer [4] | 10.7 |
| Total | 100 |
| Ratio of pure melamine/formaldehyde resins to perfume oil [5] | 0.057 |

[a] See table 4) (perfume 1B)
[1] Takenate ® D110N (75% active solution in ethyl acetate)
[2] Alcapsol from Ciba, 20% solution in water
[3] 90/10 blend of Cymel 385 & Cymel 9370 from Cytec, both 70% solution in water
[4] Salcare SC60 from Ciba, 3% solution in water
[5] = pure melamine/formaldehyde resin (70% of quantity used in[2])/quantity of perfume oil

TABLE 4

Composition of perfume 1B

| Ingredients | % |
|---|---|
| GAMMA-UNDECALACTONE | 12.5 |
| VERDYL PROPIONATE | 9.6 |
| *EUCALYPTUS GLOBULUS* OIL | 12.5 |
| BENZYL SALICYLATE | 10.6 |
| HEXYL SALICYLATE | 19.3 |
| VERDOX ™ | 9.6 |
| BETA-IONONE | 12.5 |
| ISO-BORNYL ACETATE | 4.8 |
| CITRONITRILE | 4.8 |
| 2,4-DIMETHYL-3-CYCLOHEXENE-1-CARBALDEHYDE | 3.8 |

The oil phase was prepared by admixing a polyisocyanate (trimethylol propane adduct of xylylene diisocyanate, Takenate® D-110N, origin: Mitsui Chemicals) with a core oil composed of a perfume oil (see table 4) above). The oil phase consisted of 2% Takenate® D-110N and 98% of core oil. After encapsulation and use of the Takenate D-110N to cross-link the melamine-formaldehyde wall, the residual level of unreacted polyisocyanate in the core oil was very low and therefore the internal core of the capsule was only made of the core oil composed of a perfume oil.

To make the capsules slurry, the acrylamide and acrylic acid copolymer and the blend of the two melamine-formaldehyde resins were dissolved in water to form the water phase. Then the perfume premix oil was added into this solution and the pH was regulated to 5 with acetic acid. The temperature was raised to 90° C. for 2 hours to allow the curing of the capsules. At this point, capsules were formed, cross-linked and stable. A 3% Salcare SC60 (acrylamidopropyltrimonium chloride/acrylamide copolymer) solution in water was then added into the mixture at 80° C. and was allowed to react for 2 hours at 80° C. Then a solution of ethylene urea (50% wt in water) was added as usually done with aminoplast capsules as an agent to scavenge residual free formaldehyde. Final slurry contains about 3% w/w of ethylene urea relative to the weight of the slurry and the mixture was left to cool down to room temperature. The final pH was adjusted to 7 with sodium hydroxide.

An emulsion of the following composition was spray-dried in a spray-drier Büchi (origin: Switzerland) (with an air inlet temperature set to 215° C. and a throughput set to 500 ml per hour. The air outlet temperature was of 105° C.) to obtain spray-dried granules having the following composition (see Table 5).

TABLE 5

Composition of spray-dried granules B

| Ingredients | |
|---|---|
| | Emulsion B |
| Modified starch[1] | 12.5% |
| Maltose[2] | 7.9% |
| Citric Acid | 1% |
| Tripotassium Citrate | 1.9% |
| Microcapsules slurry[3] | 8.9% |
| Free Perfume A[4] | 11% |
| Water | 56.9% |
| | Granule B |
| Modified starch | 31.6% |
| Maltose | 20.9% |
| Citric Acid | 2.6% |
| Tripotassium citrate | 4.9% |
| Perfume A | 28.1% |
| Microcapsules from slurry | 9.8% |
| Silica | 2.0% |
| Fragrance loading in powder after spray-drying | 35.8% |

[1] CapsulTM, Ingredion
[2] Maltose, Lehmann & Voss
[3] Silica, Evonik
[4] see table 2

A dry blending is carried out between granules B and talc (50:50).

Example 2

MIE Performance of Powdered Compositions

A dry blending was carried out between granules A and different fireproofing agents in different amounts to obtain Blend I, blend II and comparative blends III and IV (see table 6).

The minimal ignition energy (MIE) was measured for the different blends.

The minimum ignition energy was measured on a MIKE-3 apparatus (Cesana AG, Baiergasse 56, CH-4126 Bettingen (Basel), Switzerland). The test protocol is described in ASTM-E2019, VDI-2263, Center for Chemical Process Safety CCPS Publication G-95, Guidelines for Safe Handling of Powders and Bulk Solids © 2005 by the American Institute of Chemical Engineers, and the Operating Instructions for the MIKE-3 apparatus.
The protocol used to measure MIE is described in ASTM-E2019, VDI-2263, Center for Chemical Process Safety CCPS Publication G-95, *Guidelines for Safe Handling of Powders and Bulk Solids* © 2005 by the American Institute of Chemical Engineers, and the Operating Instructions for the MIKE-3 apparatus (manufactured by Kühner AG, Birsfelden, CH), by C. Cesana and R. Siwek).

Results are shown in the table below.

TABLE 6

| | MIE values | | | |
|---|---|---|---|---|
| Ingredient | Blend I (%) | Blend II (%) | Comparative blend III (%) | Comparative Blend IV (%) |
| Sodium Sulphate A[1] | — | — | — | 85 |
| Sodium Sulphate B[2] | — | — | 50 | — |
| Talc[3] | 50 | 70 | — | — |
| Granules A[4] | 50 | 30 | 50 | 15 |
| Minimum Ignition Energy (MIE)[5] | >300 mJ | >1000 mJ | 100-300 mJ | 100-300 mJ |

[1] Anhydrous sodium sulphate; origin Birla Cellulosic, India
[2] Anhydrous sodium sulphate; origin MSM, Spain
[3] Talc (Magnesium Silicate); origin Hi Tech Minerals & Chemicals, India
[4] see Example 1

One can conclude from Table 6 that the use of talc allows blends to be formulated with high levels of spray dried powder (50% in Blend I) compared to blend formulated with the same amount, or even greater amount of sodium sulphate that gives lower MIE values.

The invention claimed is:

1. A powdered composition comprising at least one dried granule, wherein the granule comprises a perfume oil or a flavour oil dispersed in a polymeric matrix, wherein the powdered composition contains a fireproofing agent comprising talc, wherein a weight ratio between the granule and the talc in the powdered composition is between 30:70 and 60:40; and wherein the powdered composition has a minimum ignition energy (MIE)≥300 mJ and the talc has a mean particle size between 5 and 50 microns.

2. A powdered composition comprising at least one dried granule, wherein the granule comprises:
    a polymeric matrix, and
    an oil phase comprising a perfume oil or a flavour oil, dispersed in said matrix,
    wherein a fireproofing agent comprising talc is dispersed within the polymeric matrix;
    wherein the talc has a mean particle size between 5 and 50 microns;
    wherein a weight ratio between the granule and the talc in the powdered composition is between 30:70 and 60:40; and
    wherein the powdered composition has a minimum ignition energy (MIE)≥300 mJ.

3. The powdered composition according to claim 1, wherein a totality of the perfume oil or the flavour oil is not encapsulated in core-shell microcapsules in the polymeric matrix.

4. The powdered composition according to claim 1, wherein a totality of the perfume oil or the flavour oil is encapsulated in core-shell microcapsules in the polymeric matrix.

5. The powdered composition according to claim 1, wherein at least one part of the perfume oil or the flavour oil is freely dispersed in the polymeric matrix and at least one part of the perfume oil or the flavour oil is encapsulated in core-shell microcapsules in the polymeric matrix.

6. The powdered composition according to claim 1, wherein the powdered composition further comprises an anti-caking agent.

7. The powdered composition according to claim 1, wherein the polymer matrix is a water-soluble polymer matrix selected from the group consisting of maltodextrin, modified starch, and mixtures thereof.

8. The powdered composition according to claim 1, wherein the weight ratio between the granule and the talc is comprised between 40:60 and 55:45.

9. The powdered composition according to claim 1, wherein the powdered composition further comprises an anti-caking agent comprising silica.

10. The powdered composition according to claim 1, wherein the granule has a mean particle size between 35 and 300 microns.

11. A powdered consumer product, comprising the powdered composition as defined in claim 1.

12. A powdered consumer product in a form of a dry shampoo, talcum powder, powder detergent, detergent beads, solid scent booster, cat litter, powder hair dye, antiperspirant composition, deodorant composition, comprising the powdered composition as defined in claim 1.

\* \* \* \* \*